United States Patent [19]

Menschik

[11] Patent Number: 4,911,723
[45] Date of Patent: Mar. 27, 1990

[54] ARTIFICIAL HIP JOINT

[76] Inventor: Alfred Menschik, Holzgasse 11, A-3400 Klosterneuburg, Austria

[21] Appl. No.: 216,342

[22] Filed: Jul. 7, 1988

[30] Foreign Application Priority Data

Jul. 9, 1987 [AT] Austria .................. 1738/87

[51] Int. Cl.$^4$ .......................... A61F 2/36; A61F 2/32
[52] U.S. Cl. ........................................ 623/23; 623/22
[58] Field of Search ..................... 623/16, 18, 22, 23

[56] References Cited

U.S. PATENT DOCUMENTS

| Re. 32,488 | 9/1987 | Gustilo et al. | 623/23 |
| 4,221,623 | 9/1980 | Heissler et al. | 623/23 |

Primary Examiner—Richard J. Apley
Assistant Examiner—David J. Isabella
Attorney, Agent, or Firm—Collard, Roe & Galgano

[57] ABSTRACT

The invention relates to an artificial hip joint, in which the surfaces of both the socket and the ball of the joint are in the form of rotational bodies (rotational surfaces) deviating from the normal spherical shape. The rotational surfaces are in the form of Pascal's curve or screw rather than being spherical. In addition, provision is made such that an angular deviation $\alpha$ is present between the axis of the femoral throat of the thigh and the rotary axis of the ball of the joint when viewed from the top, such deviation preferably equal to 10.7°±3°.

4 Claims, 2 Drawing Sheets

ARTIFICIAL HIP JOINT

BACKGROUND OF THE INVENTION

1. Field of the Invention

The invention relates to an artificial hip joint for replacing the natural ball and/or natural socket of the joint, whereby the artificial surfaces of the joint are embodied in the form of rotary surfaces.

2. Description of the Prior Art

It is known to manufacture artificial hip joints with the surfaces of the joint substantially embodied in the form of spherical surface both in the socket and in the ball of the joint. Although such hip joints have offered a good substitute for hip joints which had been altered pathologically, or which had been poor from the date of birth, implantations of artificial hip joints have often caused walking problems and other impairments in the patients having them.

SUMMARY OF THE INVENTION

It is an object of the present invention to provide a hip joint which eliminates such problems and to provide a hip joint superior to those presently found in the artificial hip joints field.

It is a further object of the invention to provide an artificial hip joint having a ball and socket having mating surfaces which are non-spherical and which inherently avoid out of equilibrium positions.

Accordingly, this objective is accomplished in the present invention wherein the surface of the socket of the joint, or the surface of the ball of the joint is embodied in the meridian section as a Pascal's curve (screw). The result of such an embodiment is that a reset moment occurs with each deviation between the axes of rotation of the socket and the ball of the joint. This results in that labile or unstable positions of equilibrium are avoided, disregarding the one single position in which the axes of the socket and ball of the joint are aligned. This permits the patient with an artificial hip joint implant to move with greater facility with the joint according to the invention, as compared with conventional artificial hip joints where almost every position is practically a labile position of equilibrium.

In a first embodiment, the design of the meridian section of the surface of the socket of the joint is in the form of a stretched Pascal's curve, in which case the meridian section of the surface of the ball of the joint is preferably a Pascal's curve with a loop.

In a second embodiment of the hip joint according to the present invention, the meridian section of the surface of the socket of the joint and the meridian section of the surface of the ball of the joint are Pascal's curves with interexchanged parameters, i.e., if the meridian section of the ball of the joint follows the relation $r = a + b \cos\phi$, the meridian section of the socket of the joint follows the relation $r' = b + a \cos\phi$. In these relationships, $r$ and $r'$ and $\phi$ are the polar coordinates of a point of the meridian section of the ball of the joint and socket of the joint, respectively; $\phi$ is the angle between the axis of symmetry of the Pascal's curve and the radius vector at a point of the curve, and a and b are the predetermined parameters. The ratio of the two parameters (a/b) is preferably <1. Characteristic values of the parameters are 18.75 mm for parameter a, and 21.5 mm for parameter b.

In a further embodiment of the present invention, provision is made for an angular deviation to be present between the axis of the femoral throat and the rotary axis of the ball of the joint (viewed from the top). This deviation preferably amounts to 10.7°±3°. Such an embodiment offers that dead positions between the pelvis and the femur are avoided, and that a reset moment is always acting on the femur. With the embodiment of the artificial hip joint according to the present invention, the axis of rotation of the ball of the joint extends through the axis of the femoral shaft, whereas the axis of the femoral throat extends ventrally past the axis of the femoral shaft.

Although the embodiments of the invention are used with special benefits for artificial hip joints in which the surface of the socket or the surface of the ball of the joint is embodied in the meridian section in the form of a Pascal's curve (screw), in particular, i hip joints having the afore-mentioned features, the embodiment of the invention can be used also with artificial hip joints in which the ball and/or socket of the joint are embodied in the conventional (spherical) form, with the advantage that dead positions between the pelvis and the femur are avoided Other objects and features of the present invention will become apparent from the following detailed description considered in connection with the accompanying drawings, which disclose several embodiments of the invention. It is to be understood that the drawings are to be used for the purpose of illustration only, and not as a definition of the limits of the invention.

BRIEF DESCRIPTION OF THE DRAWINGS

In the drawings, wherein similar reference characters denote similar elements throughout the several views.

DESCRIPTION OF THE PREFERRED EMBODIMENTS

Figure 1:
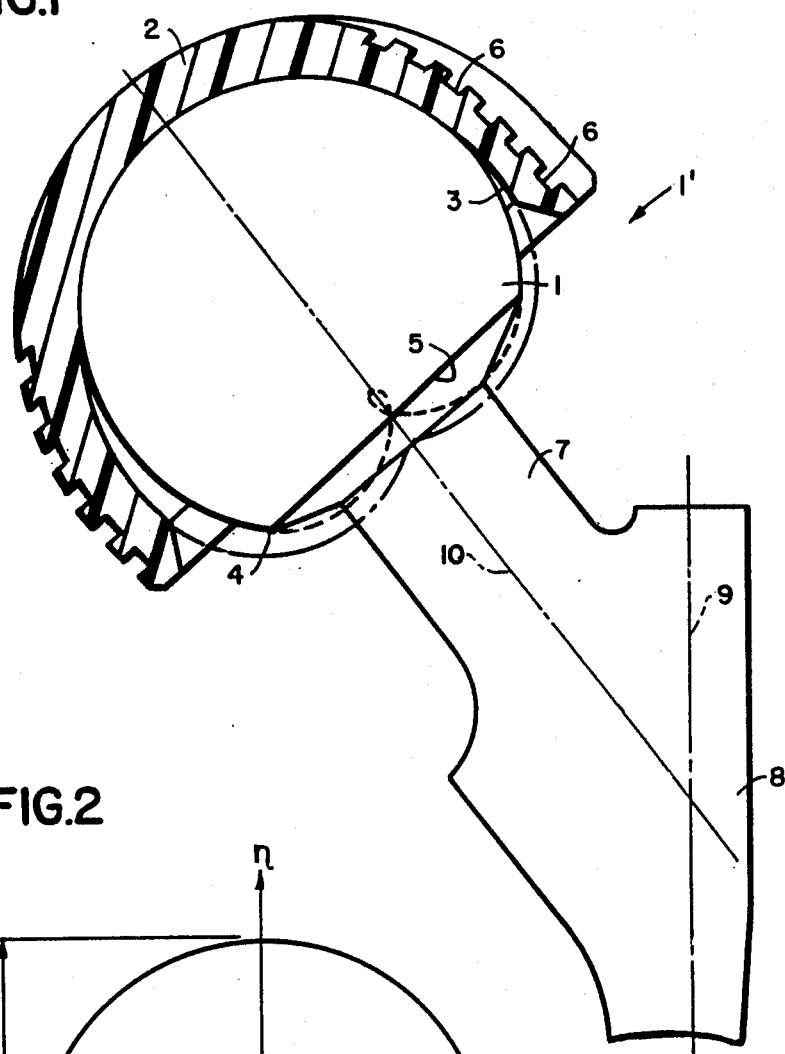
FIG. 1 is an axial cross-sectional view through a hip joint designed according to the present invention, such joint consisting of a ball and a socket.
Figure 2:
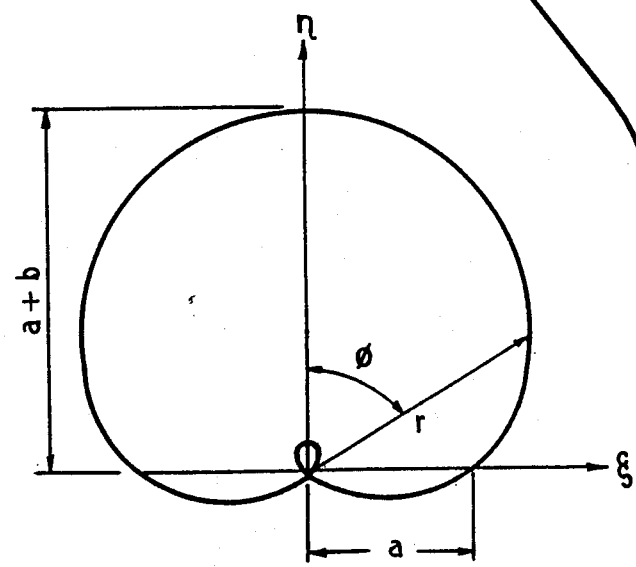
FIG. 2 is a diagram explaining the mathematical relationship inherent in the hip joint of FIG. 1.
Figure 3:
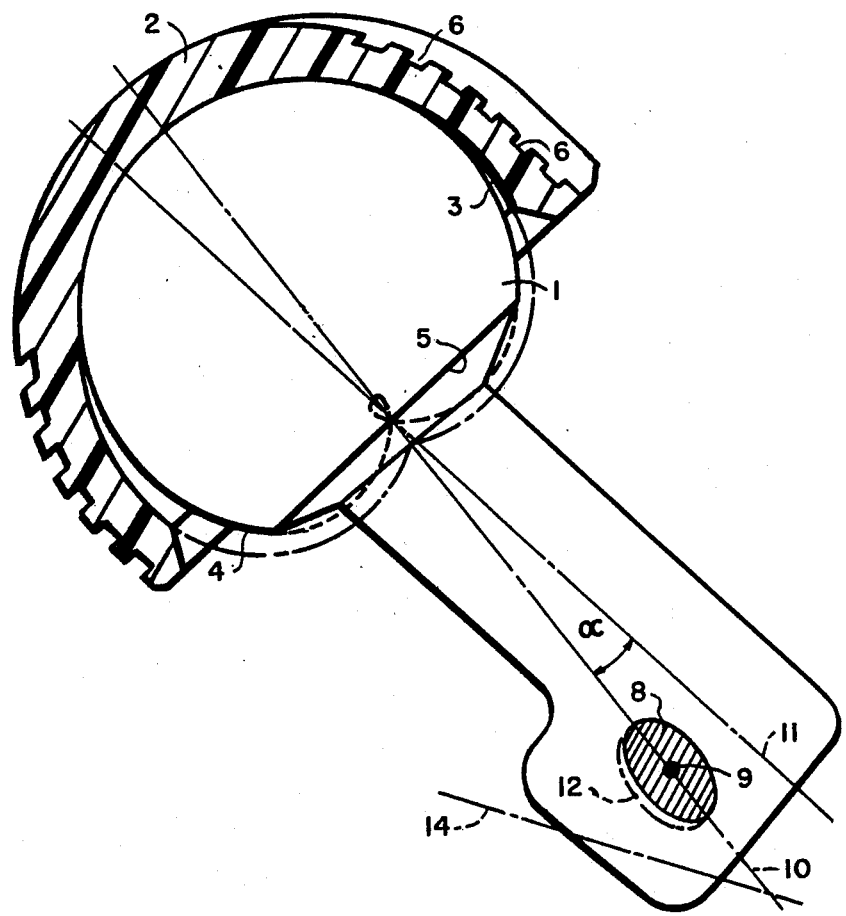
FIG. 3 is a top view of the hip joint shown in FIG. 1, with a sectional view of the socket of the joint.

Referring to FIGS. 1-3, there is shown an artificial hip joint generally denoted as 1' having a ball 1 and a socket 2. The configuration of ball 1 and socket 2 of joint 1' are in the form of rotary bodies or rotational surfaces, whereby both a surface 3 of socket 2 of the joint and a surface 4 of ball 1 of joint 1' have a meridian section formed by a Pascal's curve (Pascal's screw). The meridian section of surface 4 of ball 1 is embodied in the form of a Pascal's curve with a loop, as shown in FIG. 1. Of course, only the part of the Pascal's curve which is arranged above the throat circle 5 is used, such circle being disposed perpendicular to the axis of rotation and extending through the double point of the Pascal's curve. The meridian section of surface 3 of socket 2 of joint 1' is a stretched Pascal's curve, i.e., a curve having an indentation disposed on the axis of symmetry. The meridian section of surface 3 of socket 2 and the meridian section of surface 4 of ball 1 of the joint 1' are Pascal's curves with inter-exchanged parameters.

Referring to FIG. 2, there is shown a Pascal's screw with a loop. In the polar coordinates, the points of Pascal's curve follow the equation $r = a + b \cos\phi$. If a $\xi/\eta$ coordinate system is placed through the Pascal's curve in such a way that the η-axis coincides with the axis of symmetry of the Pascal's curve and the origin of the coordinate system coincides with the double point of the Pascal's curve, the parameters a and a+b are fixed as axial segments of the Pascal's curve, whereby the angle φ as the angle of each radius vector r is measured against the axis of symmetry (η-axis).

Now, if the meridian section of joint socket 2 follows the relation of r'=b+a cos φ, the meridian section of the ball of the joint follows the relation r=a+b cos φ. This results in that both the meridian section of socket 2 and the meridian section of the ball 1 have the same sectional size on the axis of symmetry, namely a +b. On the axis extending perpendicular thereto, the meridian section of ball 1 has the axial segment a, whereas the meridian section of the socket 2 has the axial segment b. The section is made in a way such that b>a. Preferred values are 18.75 mm for a, and 21.5 mm for b.

In the embodiments shown of FIGS. 1-3, socket 2 of the joint is made from plastic material, with several grooves 6 being arranged on the outer jacket, such grooves 6 extending in the circumferential direction perpendicular to the axis of rotation and serving the purpose of anchoring the socket of the joint in the pelvis by means of a suitable cement (plastic adhesive). Ball 1 of the joint of the embodiment shown in FIGS. 1-3 is made from one piece together with a throat 7 and a shaft 8, the latter being implanted in the femur. However, it is possible to also plug ball 1 of the joint over a lug, of which the axis coincides with the axis of rotation of ball 1, such lug and the shaft 7 forming one piece. In the latter case, the ball 1 maybe made from plastic as well.

Referring to FIG. 3, there is shown that an angular deviation α is present between the axis 11 of the swivel throat and the rotary axis 10 of ball 1. Such axis 10 and axis 9 of the shaft 8 of the thigh or prosthesis being disposed in the same plane. Preferably, such deviation comes to 10.7°+3°. The bone marrow space 12 in the femur, in which shaft 8 is implanted, is shown in FIG. 3 by a dash-dotted line. Rotary axis 10 of ball 1 and axis 9 of shaft 8 form an angle of about 126°. When viewed from the top (FIG. 3), rotary axis 10 of ball 1 and the posterior femoral condylar axis 14 jointly form an angle of about 34°. The angular positions of axes 10 and 11 (FIG. 3) and 9 and 10 (FIG. 1), respectively, as shown in the drawings, may be used also with artificial hip joints of which the ball or socket of the joint has the conventional (e.g., spherical) shape.

While only several embodiments and examples of the present invention have been described, it is obvious that aany changes and modifications may be made thereunto, without departing from the spirit and scope of the invention.

What is claimed is:

1. An artificial hip joint for replacing one or both of the natural ball and the natural socket of the joint comprising:
   an artificial ball defining an outer notational surface in the shape of, in meridian section, a Paschal's curve; and
   an artificial socket defining an inner notational surface in the shape of, in meridian section, a Pascal's curve;
   wherein the meridian section of the ball of the joint follows the relation r=a+b cos φ, the meridian section of the socket of the joint follows the relation r'=b+a cos φ, wherein r and r', respectively, and φ are the coordinates of a point of the meridian section of the ball of the socket of the joint, respectively, φ is the angle between the axis of symmetry of the Pascal's curve and the radius vector relative to a point of the curve, and a and b are predetermined parameters, wherein (a/b) is <1.

2. The artificial hip joint as set forth in claim 1, wherein the meridian section of the rotational surface of the ball of the joint is a Pascal's curve with a loop.

3. The artificial hip joint as set forth in claim 1, wherein the meridian section of the rotational surface of the socket of the joint is a stretched Pascal's curve.

4. The artificial hip joint as set forth in claim 1 wherein a is 18.75 mm and b is 21.5 mm.

* * * * *